United States Patent
Clark et al.

(10) Patent No.: US 9,579,641 B2
(45) Date of Patent: Feb. 28, 2017

(54) ARYL PHOSPHINES WITH FUSED RING ORTHO-ALKOXY SUBSTITUTION

(71) Applicant: Dow Global Technologies LLC, Midland, MI (US)

(72) Inventors: Thomas P. Clark, Midland, MI (US); Heather A. Spinney, Midland, MI (US); Sarah E. House, Lake Jackson, TX (US); John R. Briggs, Midland, MI (US); Clark H. Cummins, Midland, MI (US); Jessica L. Klinkenberg, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/899,715

(22) PCT Filed: Jun. 18, 2014

(86) PCT No.: PCT/US2014/042846
§ 371 (c)(1),
(2) Date: Dec. 18, 2015

(87) PCT Pub. No.: WO2014/205025
PCT Pub. Date: Dec. 24, 2014

(65) Prior Publication Data
US 2016/0184811 A1 Jun. 30, 2016

Related U.S. Application Data

(60) Provisional application No. 61/837,475, filed on Jun. 20, 2013.

(51) Int. Cl.
*C07D 405/00* (2006.01)
*B01J 31/24* (2006.01)
*C07F 9/50* (2006.01)
*C07F 15/00* (2006.01)
*C07F 9/655* (2006.01)

(52) U.S. Cl.
CPC ....... *B01J 31/2457* (2013.01); *B01J 31/2404* (2013.01); *B01J 31/2414* (2013.01); *B01J 31/2433* (2013.01); *C07F 9/50* (2013.01); *C07F 9/5045* (2013.01); *C07F 9/65517* (2013.01); *C07F 9/65522* (2013.01); *C07F 9/65527* (2013.01); *C07F 15/006* (2013.01); *C07F 15/008* (2013.01); *C07F 15/0073* (2013.01); *B01J 2231/20* (2013.01); *B01J 2531/824* (2013.01); *B01J 2540/10* (2013.01)

(58) Field of Classification Search
None
See application file for complete search history.

(56) References Cited

FOREIGN PATENT DOCUMENTS

WO 2013096631 6/2013

OTHER PUBLICATIONS

CAPLUS 2004 1124239.*
Tschan, et al., "Large P-P Distance Diphosphines and Their Monophosphine Analogues as Ligands in the Palladium-Catalyzed Telomerization of 1,3-Butadiene and Methanol" Organometallics, 2011, vol. 30, pp. 792-799 (8 pgs).
International Preliminary Report on Patentability for related PCT Application PCT/US2014/042846, mailed Jun. 3, 2015 (9 pgs).
International Search Report and Written Opinion for related PCT Application PCT/US2014/042846, mailed Oct. 9, 2014 (12 pgs).

* cited by examiner

*Primary Examiner* — Heidi Reese
(74) *Attorney, Agent, or Firm* — Brooks, Cameron & Huebsch, PLLC

(57) ABSTRACT

An aryl phosphine with fused ring ortho-alkoxy substitution that includes an aryl monophosphine and an aryl bi-sphosphme.

10 Claims, No Drawings

ARYL PHOSPHINES WITH FUSED RING ORTHO-ALKOXY SUBSTITUTION

This application is a National Stage Application under 35 U.S.C. §371 of International Application No. PCT/US2014/042846, filed Jun. 18, 2014 and published as WO 2014/205025 on Dec. 24, 2014, which claims the benefit to U.S. Provisional Application 61/837,475, filed Jun. 20, 2013, the entire contents of which are incorporated herein by reference in its entirety.

This disclosure relates to aryl phosphines with fused ring ortho-alkoxy substitution.

Phosphorous (P) containing compounds are ligands for a variety of transition metals, including, but not limited to titanium (Ti), copper (Cu), palladium (Pd), cobalt (Co), rhodium (Rh), ruthenium (Ru), chromium (Cr) and platinum (Pt). In particular, P containing compounds, such as aryl phosphines, which include a P atom covalently bonded to an aryl ring, are ligands for a variety of transition metal catalyzed reactions. These transition metal catalyzed reactions can include hydrogenations, ethylene carbon monoxide copolymerizations, butadiene telomerization, hydroformylation, metal (e.g., Pd) catalyzed cross coupling (e.g., Suzuki reactions, Buchwald-Hartwig coupling reactions), methoxycarbonylation of olefins, ethylene oligomerization, and olefin polymerization.

When an aryl phosphine is used as a ligand for one of these transition metal catalyzed reactions, the electronic and steric environment around the transition metal catalyst can be changed by varying the substituents on the aryl ring of the phosphine. For instance, ortho-alkoxy substitution on the aryl ring of the aryl phosphine is considered an electron donating group and has shown value for a variety of industrially relevant transformations (WO2011101504 for butadiene telomerization; J. Am. Chem. Soc. 2008, 130, 13552 for cross coupling; J. Mol. Cat. A 2007, 265, 292-305 for ethylene-carbon monoxide copolymerization). However, the placement of functional groups in the ortho-aryl position changes the steric parameters around the catalyst, which can negatively affect catalyst performance in some cases.

The present disclosure provides for the surprising discovery that an aryl phosphine with a fused ring ortho-alkoxy substitution allows for an electronic benefit associated with the ortho-alkoxy group (e.g., electron donating group) while reducing steric bulk around the catalyst compared to an alkoxy group lacking a fused ring, enabling increased performance of catalysts containing this aryl phosphine as a ligand. Increased performance can refer to higher rate of reaction, higher conversion of reagents, increased catalyst turnover number, longer catalyst lifetime, and/or improved selectivity for a desired product relative to side products.

The present disclosure provides for an aryl phosphine that includes 1 P atom bonded to the aryl group and an aryl bisphosphine that includes a first aryl phosphine that is bonded to a second phosphine via a bridging group. The present disclosure provides for, among other things, an aryl phosphine with fused ring ortho-alkoxy substitution of Formula (I):

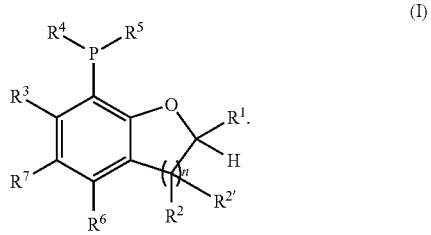

The aryl phosphine includes a fused ring ortho-alkoxy substituent on the aryl group, which is covalently bonded to the aryl group through an oxygen atom at the ortho-position and a carbon atom at the adjacent meta-position relative to the phosphorous bond to the aryl group. The fused ring ortho-alkoxy substituent forms a ring structure, as shown in Formula (I), where n is an integer in a range from 1 to 3, thus providing a cyclic structure having a 4 to 6 carbon anatomy and an oxygen atom. Each $R^2$ and $R^{2'}$ is independently selected from the group consisting of H, a substituted or unsubstituted alkyl having 1 to 18 carbons, and a substituted or unsubstituted phenyl ring. $R^1$ and $R^3$ are selected from the group consisting of H, a substituted or unsubstituted alkyl having 1 to 18 carbons, and a substituted or unsubstituted phenyl ring.

$R^4$ and $R^5$ can be independently selected from the group consisting of H, a substituted or unsubstituted alkyl having 1 to 18 carbons, a substituted or unsubstituted cycloalkyl having 3 to 18 carbons and preferably having 3 to 10 carbons, a halogen, an aryl, and a substituted or unsubstituted phenyl ring. Halogens are selected from the group consisting of chlorine (Cl), bromine (Br), iodine (I), and fluorine (F). When $R^4$ and/or $R^5$ is an alkyl, $R^4$ and $R^5$ can be independently selected from the group consisting of methyl, ethyl, n-propyl, isopropyl, n-butyl, sec-butyl, isobutyl, t-butyl. When $R^4$ and/or $R^5$ is a cycloalkyl, $R^4$ and $R^5$ can be independently selected from the group consisting of adamantyl and cyclohexyl. $R^4$ and $R^5$ can be independently selected from an aryl group consisting of a substituted or unsubstituted phenyl and substituted or unsubstituted biphenyl.

$R^6$ and $R^7$ are independently selected from the group consisting of H, a substituted or unsubstituted alkyl having 1 to 18 carbons, a substituted or unsubstituted cycloalkyl having 3 to 18 carbons, a halogen, and a substituted or unsubstituted phenyl ring. Halogens are selected from the group consisting of Cl, Br, I, and F.

For the substituted structures of $R^1$, $R^2$, $R^{2'}$, $R^3$, $R^4$, $R^5$, $R^6$, or $R^7$, substituents can include functional groups containing heteroatoms selected from the group consisting of oxygen (O), nitrogen (N), halogens, sulfur (S), boron (B), P, and silicon (Si). For instance, functional groups can include $F_3C-$, $FCH_2O-$, $F_2HCO-$, $F_3CO-$, $R_3Si$, $B(OR)_2$, RO, RS, RS(O), $RS(O)_2$, $R_2P$, $R_2N$, $R_2C=N$, NC, RC(O)O, ROC(O), RC(O)N(R), or $R_2NC(O)$.

$R^3$ and $R^7$ can also be combined to form a cyclic structure, as shown in Formula (II):

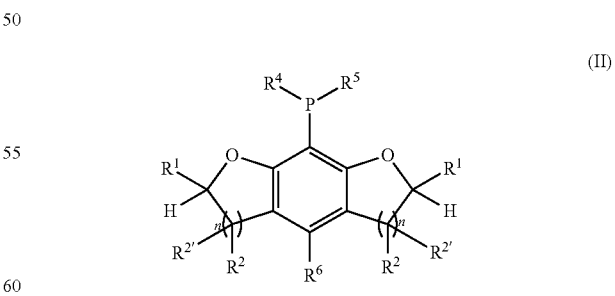

When $R^3$ and $R^7$ are combined to form the ring structure of Formula (II), $R^3$ is an oxy and $R^7$ is an alkyl, where n is an integer, as discussed herein, $R^1$, $R^2$, and $R^{2'}$ are independently selected from the groups discussed herein. As such, ortho-alkoxy groups can be bound to either side of the aryl ring in Formula (I).

$R^4$ and $R^5$ can be independently selected from the group consisting of methyl, ethyl, n-propyl, isopropyl, n-butyl, sec-butyl, isobutyl, t-butyl, adamantyl, phenyl, biphenyl, and cyclohexyl. The P atom of the aryl phosphine, together with $R^4$ and $R^5$ can form a 5-, 6-, or 7-membered ring. For instance, the P atom of the aryl phosphine can be a member of a ring structure formed from carbons in a range from 4 to 6. In addition, the ring structure can include heteroatoms such as those discussed herein.

$R^4$ can be independently selected from the group consisting of Formulae (III) to (XI):

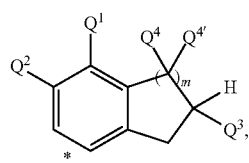

(III)

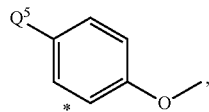

(IV)

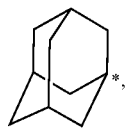

(V)

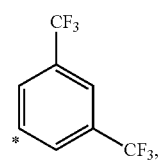

(VI)

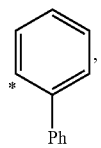

(VII)

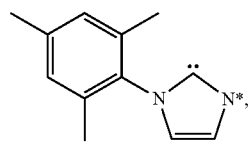

(VIII)

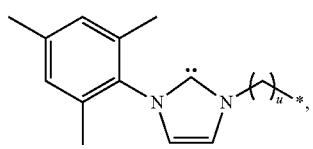

(IX)

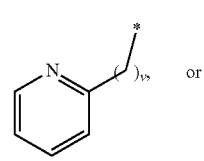

(X)

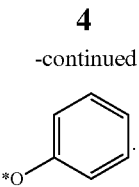

(XI)

In Formula (III), m is 1 or 2 and thus the ring bonded to the aryl group can include 4 or 5 carbons. In Formula (III), $Q^1$ and $Q^2$ are independently selected from the group consisting of H, a substituted or unsubstituted alkyl having 1 to 18 carbons, a substituted or unsubstituted cycloalkyl having 3 to 18 carbons, a halogen, and a substituted or unsubstituted phenyl ring. $Q^3$ is selected from the group consisting of H, a substituted or unsubstituted alkyl having 1 to 18 carbons, and a substituted or unsubstituted phenyl ring. Each $Q^4$ and $Q^{4'}$ is independently selected from the group consisting of H, a substituted or unsubstituted alkyl having 1 to 18 carbons, and a substituted or unsubstituted phenyl ring.

In Formula (IV), $Q^5$ is selected from the group consisting of H, a substituted or unsubstituted alkyl having 1 to 18 carbons, a substituted or unsubstituted cycloalkyl having 3 to 18 carbons and preferably having 3 to 10 carbons, a halogen, and a substituted or unsubstituted phenyl ring. In Formula (IX), u is an integer in a range from 0 to 2; and in Formula (X), v is an integer in a range from 0 to 2.

When $R^4$ and $R^5$ are both Formula (XI), $R^4$ and $R^5$ are optionally covalently bound together at the ortho position relative to the bond between the O atom and the phenyl group in Formula (XI). For instance, when $R^4$ and $R^5$ are covalently bound together at the ortho position to the respective C atoms in Formula (XI), a ring is formed that includes a P atom of Formula (I), 2 oxygen atoms, and 4 carbon atoms, as illustrated in Formula (XLI).

Specific but non-limiting examples of Formula (I) include the following Formulae (XII) to (XXVIII), which can serve as ligands for catalytic reactions, including but not limited to butadiene ($C_4H_6$) telomerization:

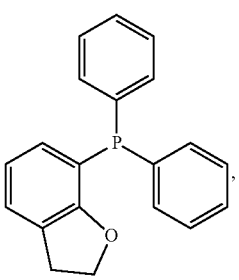

(XIV)

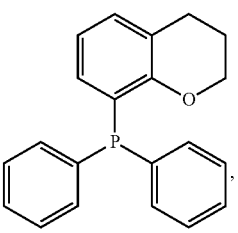

(XII)

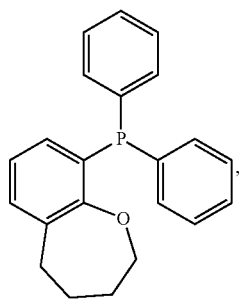
(XIII)
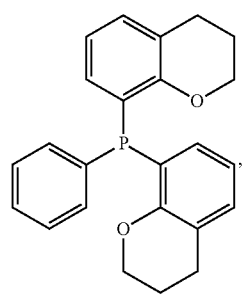
(XV)
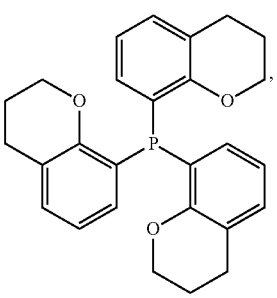
(XVI)
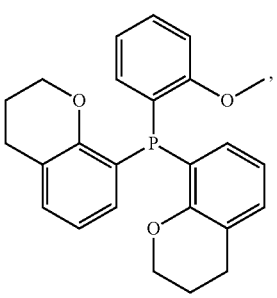
(XVII)
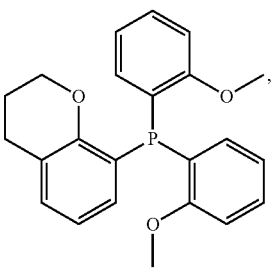
(XVIII)
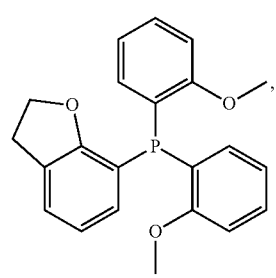
(XIX)
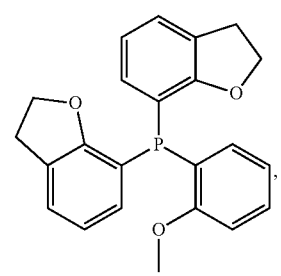
(XX)
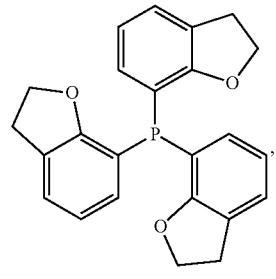
(XXI)
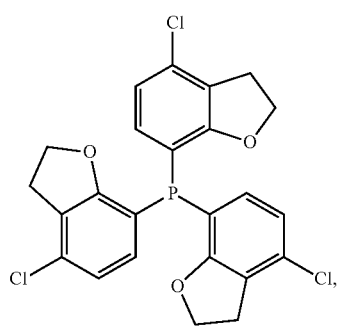
(XXII)
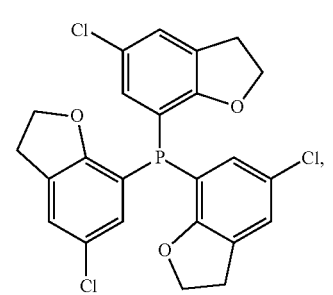
(XXIII)

(XXV) 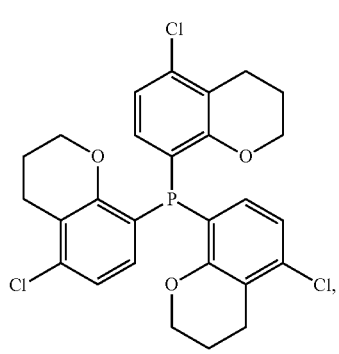
(XXVI) 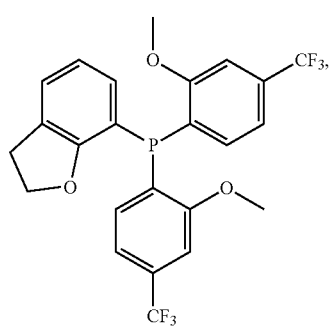
(XXVII) 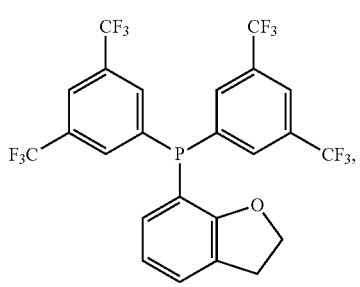
(XXVIII) 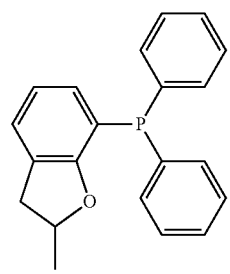
Specific but non-limiting examples of Formula (I) include the following Formulae (XXIX) to (XXXV), which can serve as ligands for catalytic reactions, including but not limited to Pd catalyzed cross coupling:
(XXIX) 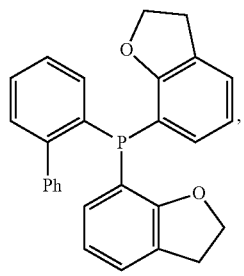
(XXX) 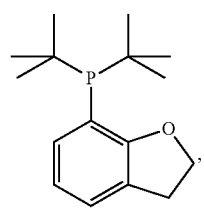
(XXXI) 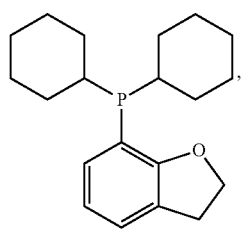
(XXXII) 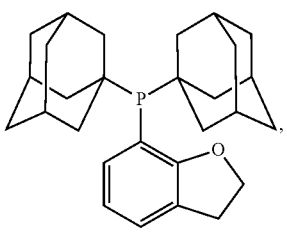
(XXXIII) 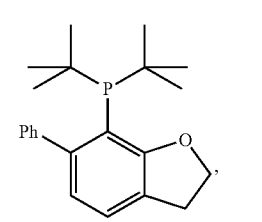
(XXXIV) 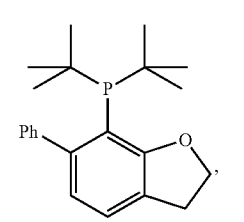

(XXXV)

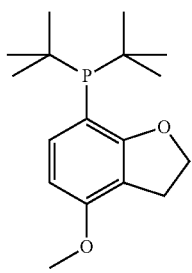

Specific but non-limiting examples of Formula (I) include the following Formulae (XXXVI) to (XLII), which can serve as ligands for catalytic reactions, including but not limited to methoxycarbonylation and/or hydroformylation:

(XXXVI)

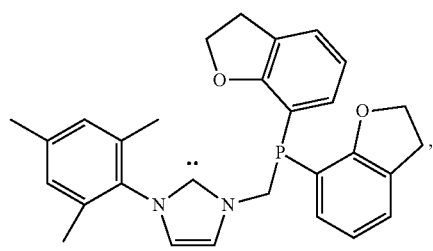

(XXXVII)

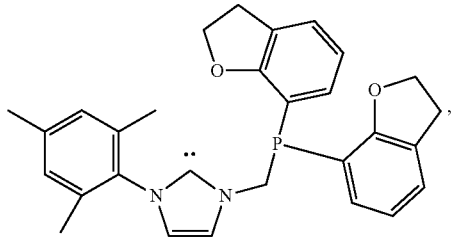

(XXXVIII)

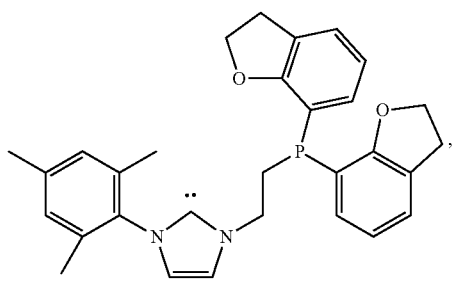

(XXXIX)

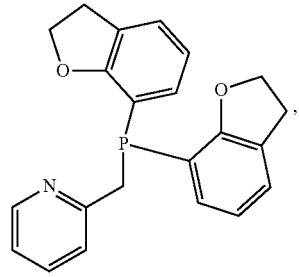

(XL)

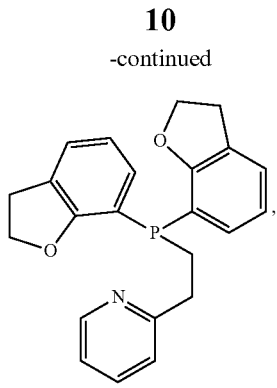

(XLI)

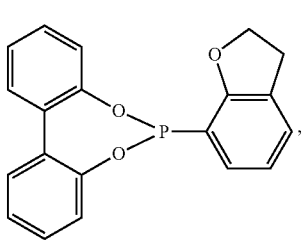

(XLII)

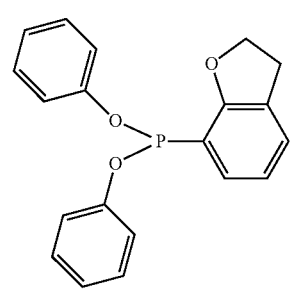

Specific but non-limiting examples of Formula (I) include the following Formula (XLIII), which can be used as a synthetic precursor for the synthesis of other ligands:

(XLIII)

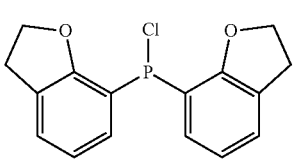

As discussed herein, the aryl phosphine can be an aryl bisphosphine, where a first aryl phosphine is bonded to a second phosphine via a bridging group. For instance, $R^5$ can be a bridging group that includes an aromatic ring and connects the aryl phosphine of Formula (I) to a second aryl phosphine of Formula (I). $R^5$ can be selected from the group consisting of Formulae (XLIV) to (LIX):

(XLIV)

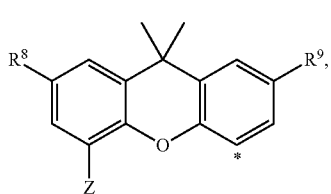

US 9,579,641 B2

11
-continued (XLVI)
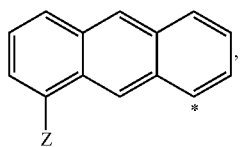

(XLV)
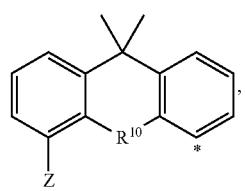

(XLVII)
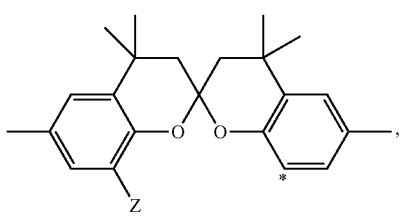

(XLIX)
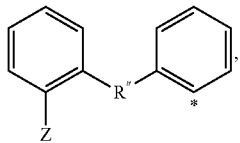

(XLVIII)
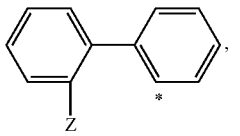

(L)
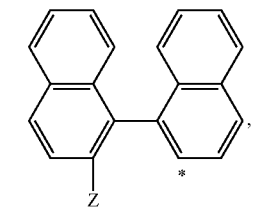

(LI)
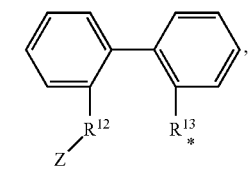

(LII)
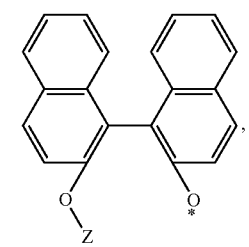

12
-continued (LIII)
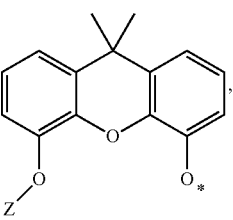

(LIV)
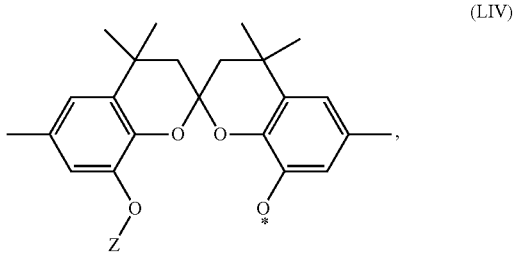

(LVII)
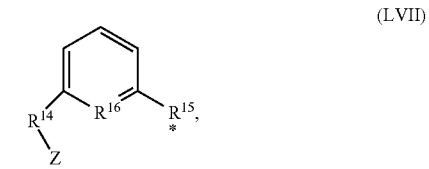

(LV)
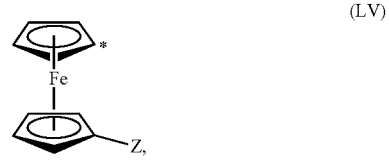

(LVI)

(LVIII)
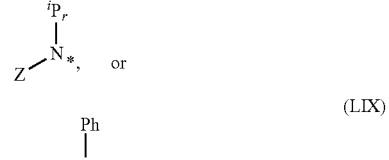

or (LIX)
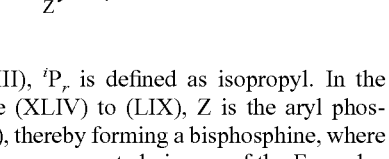

In Formula (LVIII), $^iP_r$ is defined as isopropyl. In the preceding Formulae (XLIV) to (LIX), Z is the aryl phosphine of Formula (I), thereby forming a bisphosphine, where two aryl phosphines are connected via one of the Formulae (XLIV) to (LIX). When $R^5$ is the bridging group, $R^4$ can be, but is not limited to, Formula (III). $R^8$ and $R^9$ are independently selected from H and an alkyl having 4 carbons. $R^{10}$ is selected from the group consisting of C and S. $R^{11}$ is selected from the group consisting of O and S. $R^{12}$, $R^{13}$, $R^{14}$ and $R^{15}$ are each independently selected from the group consisting of C and O. $R^{16}$ is selected from the group consisting of N and C, with the proviso that when $R^{16}$ is N then $R^{14}$ and $R^{15}$ are C.

Specific examples of Formula (I) include the following Formulae (LX) to (LXXVI), which can serve as ligands for methoxycarbonylation and/or hydroformylation:

(LX)
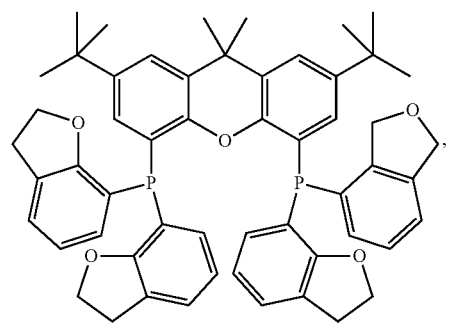
(LXI)
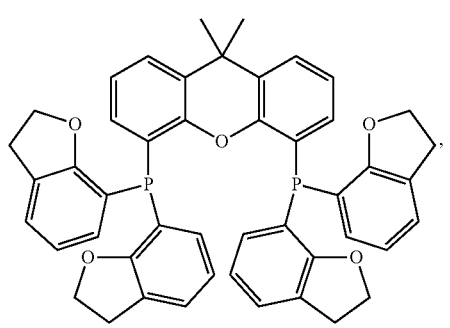
(LXII)
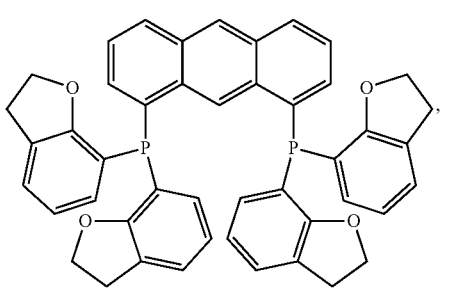
(LXIII)
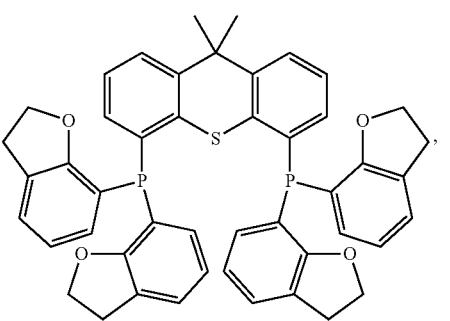
(LXIV)
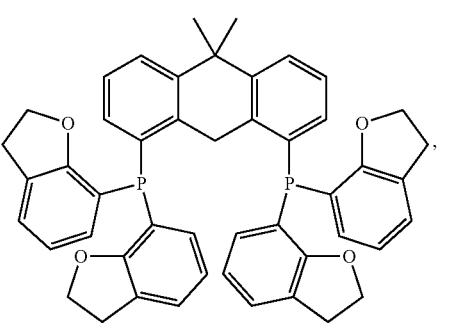
-continued
(LXV)
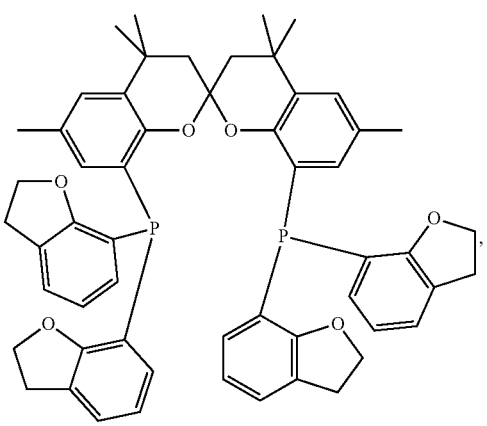
(LXVI)
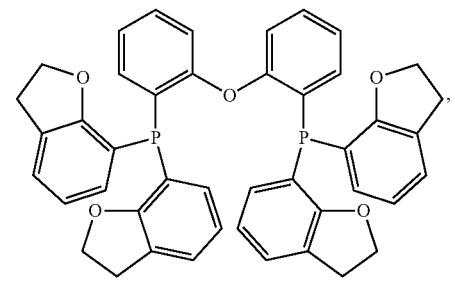
(LXVII)
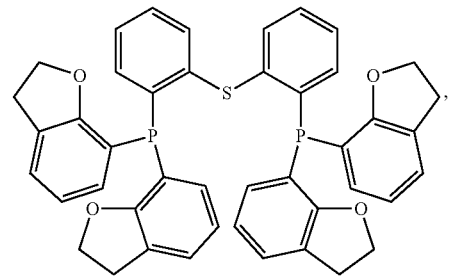
(LXVIII)
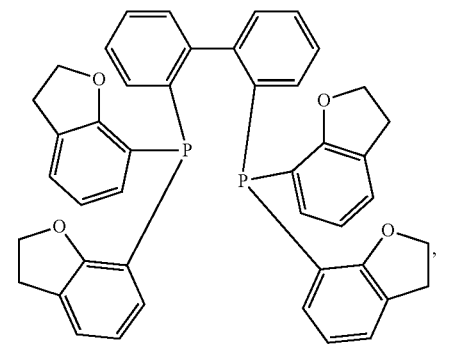

(LXIX)
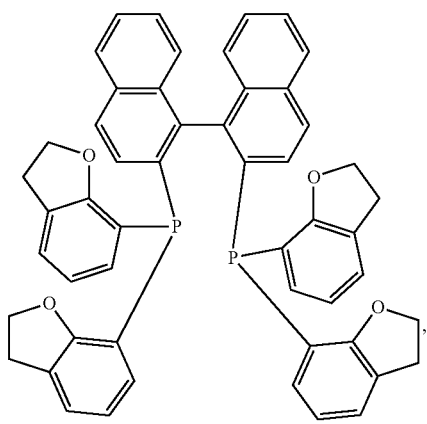
(LXX)
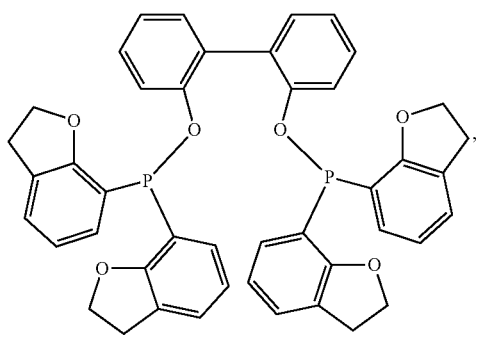
(LXXI)
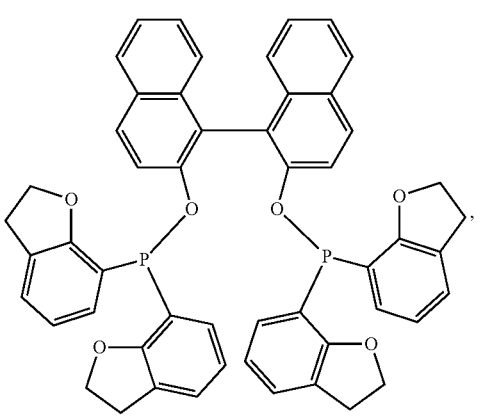
(LXXII)
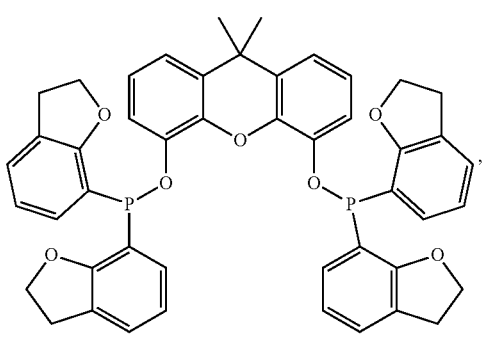
(LXXIII)
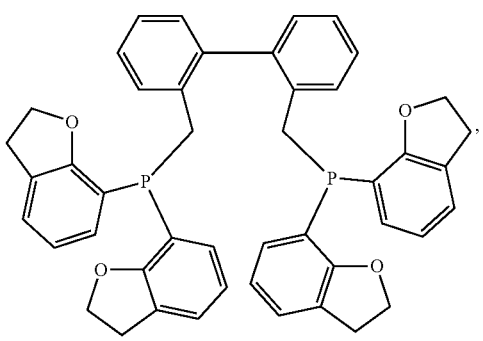
(LXXIV)
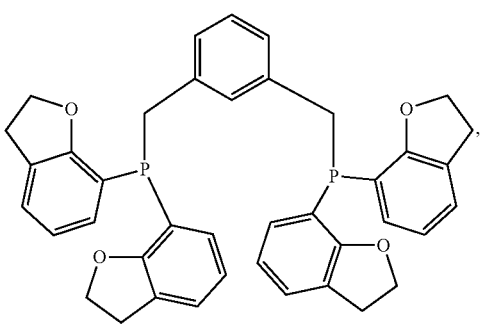
(LXXV)
(LXXVI)
A specific example of Formula (I) includes the following Formula (LXXVII), which can serve as a ligand for ethylene oligomerization:

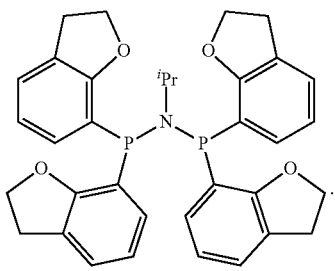

(LXXVII)

R⁵ can be a bridging group that includes an aromatic ring and can connect the aryl phosphine of Formula (I) to a second phosphine. R⁵ and the second phosphine together can form a structure selected from the group consisting of Formulae (LXXVIII) to (LXXX):

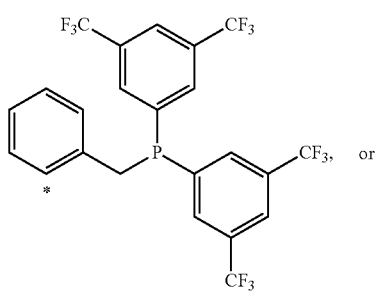

(LXXIX), or

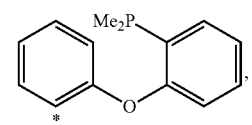

(LXXVIII)

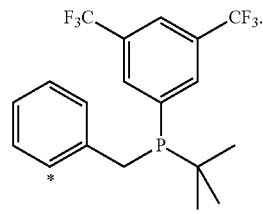

(LXXX)

Specific examples of Formula (I) include the following Formulae (LXXXI) to (LXXXIII), which can serve as ligands for methoxycarbonylation and/or hydroformylation:

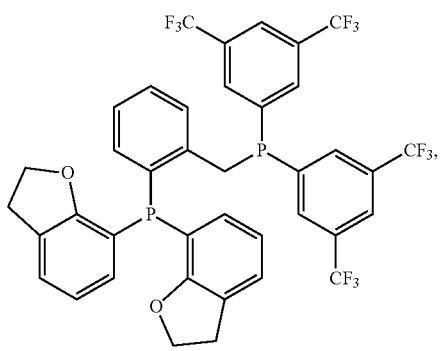

(LXXXI)

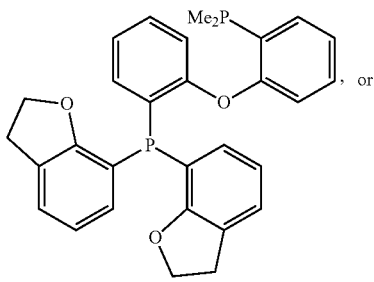

(LXXXII), or (LXXXIII)

The aryl phosphines discussed herein are ligands for a variety of transition metals. For example, the aryl phosphines discussed herein are ligands for a transition metal selected from the group consisting of titanium (Ti), copper (Cu), palladium (Pd), cobalt (Co), rhodium (Rh), ruthenium (Ru), chromium (Cr) and platinum (Pt). As such, a ligand for the present disclosure includes an aryl phosphine, as provided herein, and a transition metal selected from the group consisting of titanium (Ti), copper (Cu), palladium (Pd), cobalt (Co), rhodium (Rh), ruthenium (Ru), chromium (Cr) and platinum (Pt).

EXAMPLES

Unless otherwise noted, perform all reactions under a nitrogen atmosphere. Obtain all reactants and reagents for use in the examples, unless noted otherwise, from Sigma-Aldrich®. Use degassed reverse osmosis water (water) in all reactions, unless otherwise noted. 7-bromo-2,3-dihydrobenzofuran (synthesize according to Kerrigan, F.; Martin, C.; Thomas, G. H. Tetrahedron Lett. 1998, 39, 2219 (Kerrigan)); di-tert-butylchlorophosphine (Strem), dicyclohexylchlorophosphine (Strem), 8-bromochroman (synthesize according to Kerrigan); 9-bromo-2,3,4,5-tetrahydrobenzo[b]oxepine (synthesize according to Kerrigan); chlorobis(2-methoxyphenyl)phosphine (Alfa Aesar); allylpalladium(II) chloride dimer (Strem); toluene (Fisher).

Obtain proton, carbon-13, phosphorus-31 NMR, and ¹⁹F spectra with on one of four spectrometers: (1) Varian Mercury VXR-300, (2) Varian Mercury VX-400, (3) Varian MR-400, or (4) Varian VNMRS-500. Chemical shifts are in parts per million (ppm) relative to solvent peaks: $^1H$=7.25 for $CHCl_3$ in $CDCl_3$ and 7.16 for $C_6HD_5$ in $C_6D_6$, $^{13}C$=77.23 for $CDCl_3$ and 128.39 for $C_6D_6$.

Aryl Phosphine Including Fused Ring Ortho-Alkoxy Substitution Example (AP Ex) 1 di-tert-butyl(2,3-dihydrobenzofuran-7-yl)phosphine

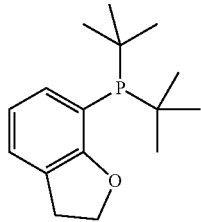 [SMILES: CC(C)(C)P(c1cccc2c1OCC2)C(C)(C)C]

Prepare AP Ex 1 as follows. Add dihydrobenzofuran (2.6 grams (g), 8.3 millimoles (mmol)) to a glass jar with a PTFE-coated stirbar. Stir the contents of the glass jar and add diethyl ether (40 milliliters (mL)) to dissolve the dihydrobenzofuran. Add n-Butyllithium (n-BuLi) (9.1 mL, 2.5 molar (M) in hexanes) dropwise to the stirred contents of the glass jar. Stir the contents of the glass jar for 22 hours (hr)s at 23° C. Remove all but 10 mL of solvent from the contents of the glass jar in vacuo. Isolate an orange oil by decanting the remaining solvent from the orange oil. Dry the orange oil under vacuum to yield aryllithium (1.47 g, 11.4 mmol).

Add the aryllithium (1.47 g) and diethyl ether (40 mL) to a second glass jar to dissolve the aryllithium. Place the contents of the second glass jar in a freezer at −40° C. for 10 minutes. Remove the second glass jar from the freezer and add di-tert-butylchlorophosphine (2.2 mL, 11.4 mmol) dropwise to the contents of the second glass jar. Stir the contents of the second glass jar for 20 hrs. Add 40 mL of water to the contents of the second glass jar to quench the reaction. Isolate the organic layer and rinse with 20 mL of water. Dry the organic layer over $MgSO_4$, filter, and place under vacuum to remove solvent. Suspend the oily white solid in 10 mL of methanol (MeOH) and place in a freezer at −40° C. for 30 minutes. Isolate the solid and dry under vacuum to yield AP Ex 1 (0.79 g) in a white solid form.

Analyze AP Ex 1 by $^1H$, $^{13}C$, and $^{31}P$ NMR spectroscopy to confirm formation. $^1H$ NMR (400 MHz, $CD_2Cl_2$) δ 7.40 (b, 1H), 7.19 (d, J=6.9 Hz, 1H)), 6.80 (t, J=6.5 Hz, 1H), 4.49 (t, J=8.4 Hz, 2H), 3.20 (t, J=8.7 Hz, 2H), 1.19 (d, $J_{P-H}$=11.8 Hz, 18H); $^{13}C$ NMR (101 MHz, $CD_2Cl_2$) δ 165.8 (b, 1C), 134.1 (s, 1CH), 127.3 (s, C), 126.1 (b, 1CH), 120.0 (s, 1CH), 117.9 (d, J=28 Hz, 1C), 70.8 (s, $1CH_2$), 32.6 (d, J=22 Hz, 2C), 30.9 (d, J=15 Hz, $6CH_3$), 30.4 (s, $1CH_2$); $^{31}P$ NMR (162 MHz, $CD_2Cl_2$) δ 51.1 (37% conformer A), 11.5 (63% conformer B). The coexistence of two conformers at 23° C. has been identified for a related structure (Organometallics 2007, 26, 3585-3596).

AP Ex 2 bis(3,5-bis(trifluoromethyl)phenyl)(2,3-dihydrobenzofuran-7-yl)phosphine

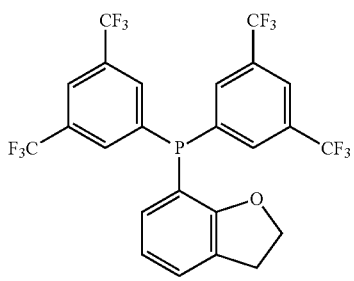 [SMILES: FC(F)(F)c1cc(P(c2cc(C(F)(F)F)cc(C(F)(F)F)c2)c2cccc3c2OCC3)cc(C(F)(F)F)c1]

Prepare AP Ex 2 as follows. Add dihydrobenzofuran (2.65 g) to a glass jar with a PTFE-coated stirbar. Stir the contents of the glass jar and add diethyl ether (40 mL) to dissolve the dihydrobenzofuran. Add n-BuLi (8.8 mL, 2.5 M in hexanes) dropwise to the stirred contents of the glass jar. Stir the contents of the glass jar for 22 hrs at 23° C. Remove 90% of the solvent from the contents of the jar in vacuo. Add hexane to the contents of the glass jar. Isolate resultant oily solid by decanting the remaining solvent from the oily solid. Rinse the oily solid with hexanes twice. Dry the oily solid under vacuum to yield a solid (1.11 g).

Suspend the solid (0.80 g) in diethyl ether (40 mL) in a second glass jar. Place the contents of the second glass jar in a freezer at −40° C. for 10 minutes. Add a solution of ether (10 mL) and bis(3,5-di(trifluoromethyl)phenyl)chlorophosphine (2.0 g) that has been previously stored in the freezer at −40° C. dropwise to the contents of the second glass jar. Maintain a reaction temperature that is cold to the touch by stopping addition of the reagents occasionally and placing the reagents back in the freezer for 5 to 10 minutes. Add a PTFE-coated stirbar to the contents of the second glass jar and stir overnight. Add 20 mL of water to the contents of the jar. Rinse the organic layer with another 20 mL of water. Isolate the organic layer, dry over $MgSO_4$, filter, and remove remaining solvent in vacuo. Isolate an orange precipitate from MeOH. Dry the orange precipitate under vacuum for 3 hours to form AP Ex 2 (0.74 g).

Analyze AP Ex 2 by $^1H$, $^{13}C$, $^{31}P$, and $^{19}F$ NMR spectroscopy to confirm formation. $^1H$ NMR (400 MHz, $CD_2Cl_2$) δ 7.92 (s, 2H), 7.88 (s, 2H), 7.86 (s, 2H), 7.37 (d, J=7.4 Hz, 1H), 7.00 (t, J=7.5 Hz, 1H), 6.92 (t, J=7.4 Hz, 1H), 4.47 (t, J=8.7 Hz, 2H), 3.24 (t, J=8.7 Hz, 2H); $^{13}C\{^1H\}$NMR (101 MHz, $CD_2Cl_2$) δ 163.2 (d, J=7 Hz, C), 140.0 (d, J=17 Hz, C), 134.4 (s, CH), 134.2 (s, CH), 134.0 (d, J=22 Hz, CH), 132.2 (qd, J=33, 6 Hz, $CCF_3$), 128.8 (s, CH), 128.8 (s, C), 123.9 (q, J=273 Hz, $CF_3$), 123.7 (m, CH), 122.1 (d, J=8 Hz, CH), 119.9 (s, C), 113.0 (d, J=13 Hz, C), 72.2 (s, $CH_2$), 30.1 (s, $CH_2$); $^{31}P\{^1H\}$NMR (162 MHz, $CD_2Cl_2$) δ −9.9 (s); $^{19}F$ NMR (376 MHz, $CD_2Cl_2$) δ −63.8 (s).

AP Ex 3

Dicyclohexyl(2,3-dihydrobenzofuran-7-yl)phosphine

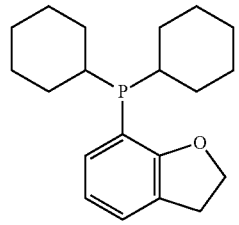 [SMILES: c1cc2c(c(P(C3CCCCC3)C3CCCCC3)c1)OCC2]

Prepare AP Ex 3 as follows to yield aryllithium (1.79 g). Repeat AP Ex 1, but with changes, add dihydrobenzofuran (2.65 g) to a glass jar. Stir the contents of the glass jar for 20 hrs at 23° C.

Add the aryllithium (1.79 g) and diethyl ether (40 mL) to a second glass jar to dissolve the aryllithium. Place the contents of the second glass jar in a freezer at −40° C. for 10 minutes. Add a PTFE-coated stirbar to the contents of the second glass jar and add dicyclohexylchlorophosphine (2.6 mL, 11.9 mmol) while stirring. Stir the contents of the second glass jar overnight at 23° C. Add 30 mL of water to the contents of the second glass jar to quench the reaction.

Isolate the organic layer and rinse with 20 mL of water. Dry the organic layer over MgSO$_4$, filter, and place under vacuum to remove solvent. Add hot (~50° C.) MeOH to the contents of the second glass jar to suspend oil. Decant the hot MeOH from the oil. Add hot (~50° C.) MeOH again to the contents of the second glass jar to suspend the oil. Decant the hot MeOH from the oil and cool the contents of the second glass jar in a freezer at −40° C. to produce AP Ex 3 (0.69 g) in a solid form.

Analyze AP Ex 3 by $^1$H, $^{13}$C, and $^{31}$P NMR spectroscopy to confirm formation. $^1$H NMR (400 MHz, CD$_2$Cl$_2$) δ 7.18 (m, 2H), 6.82 (t, J=7.4 Hz, 1H), 4.52 (t, J=8.8 Hz, 2H), 3.19 (t, J=8.7 Hz, 2H), 2.11 (m, 2H), 1.55-1.95 (m, 10H), 0.95-1.4 (m, 10H); $^{13}$C{$^1$H}NMR (101 MHz, CD$_2$Cl$_2$) peaks not identified δ 164.44, 164.37, 134.80, 134.62, 127.12, 125.97, 120.40, 120.34, 116.31, 116.09, 71.13, 33.34, 33.22, 31.35, 31.17, 30.30, 30.12, 30.04, 27.87, 27.74, 27.67, 27.12; $^{31}$P{$^1$H}NMR (162 MHz, CD$_2$Cl$_2$) 6-5.3 (s).

AP Ex 4 chroman-8-ylbis(2-methoxyphenyl)phosphine

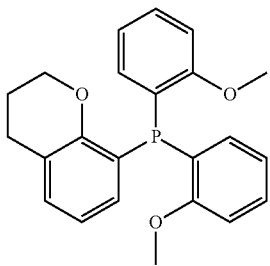 [SMILES: COc1ccccc1P(c1ccccc1OC)c1cccc2c1OCCC2]

Prepare AP Ex 4 as follows. Add 8-bromochroman (407 mg, 1.91 mmol) in dry tetrahydrofuran (THF, 10 mL) cooled in a dry ice/acetone bath to a glass jar with a PTFE-coated stirbar. Stir the contents of the glass jar and add n-BuLi (2.5M in hexanes, 0.76 mL, 1.9 mmol) dropwise. Stir the contents of the glass jar at −78° C. for 1.5 hrs. Add a suspension of chlorobis(2-methoxyphenyl)phosphine (482 mg, 1.72 mmol) in dry THF (15 mL) over the course of 10 minutes (min). Allow the contents of the glass jar to warm to 23° C. Stir the contents of the glass jar for 2 hrs at 23° C. and remove volatiles with a rotary evaporator. Quench the reaction with water (10 mL) and wash with dichloromethane (DCM). Dry the organic layer over MgSO$_4$, filter, and remove volatiles with a rotary evaporator. Add the organic layer, warm ethanol (55 mL, 50° C.), and DCM (8 mL) to a second glass jar to recrystallize the organic layer. Collect 2 crops of crystals from mother layer to yield AP Ex 4 (359 mg, 55% yield) in crystalline form.

Analyze AP Ex 4 by $^1$H, $^{13}$C, and $^{31}$P NMR spectroscopy to confirm formation. $^1$H NMR (400 MHz, CDCl$_3$) δ 7.32 (t, J=7.7 Hz, 2H), 7.03 (d, J=7.5 Hz, 1H), 6.94-6.77 (m, 4H), 6.71 (t, J=5.6 Hz, 3H), 6.53-6.42 (m, 1H), 4.10 (apparent t, J=5.0 Hz, 2H), 3.75 (s, 6H), 2.81 (t, J=6.4 Hz, 2H), 1.95 (dt, J=11.4, 5.7 Hz, 2H); $^{13}$C NMR (101 MHz, CDCl$_3$) δ 161.61 (d, J=16.8 Hz), 133.84 (s), 131.54 (s), 130.38 (s), 129.80 (s), 124.93 (d, J=13.5 Hz), 123.63 (d, J=12.8 Hz), 120.81 (s), 119.98 (s), 110.18 (s), 66.59 (s), 55.76 (s), 25.07 (d, J=1.7 Hz), 22.31 (s); $^{31}$P NMR (162 MHz, CDCl$_3$) δ −38.86 (s).

AP Ex 5

2,3-dihydrobenzofuran-7-yl)diphenylphosphine

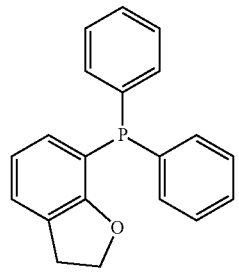 [SMILES: c1ccc(P(c2ccccc2)c2cccc3c2OCC3)cc1]

Repeat AP Ex 4, but with changes: add 7-bromo-2,3-dihydrobenzofuran (200 mg, 1.0 mmol), rather than 8-bromochroman and add chlorodiphenylphosphine (0.19 mL, 1.0 mmol), neat, rather than chlorobis(2-methoxyphenyl)phosphine to produce AP Ex 5 in white powder form (129 mg, 45% yield).

Analyze AP Ex 5 by $^1$H, $^{13}$C, and $^{31}$P NMR spectroscopy to confirm formation. $^1$H NMR (400 MHz, CDCl$_3$) δ 7.49-7.34 (m, 10H), 7.26 (dd, J=7.2, 0.8 Hz, 1H), 6.84 (t, J=7.5 Hz, 1H), 6.69 (dd, 1H), 4.59 (t, J=8.7 Hz, 2H), 3.26 (t, J=8.7 Hz, 2H); $^{13}$C NMR (101 MHz, CDCl$_3$) δ 162.44 (d, J=16.7 Hz), 136.06 (d, J=10.0 Hz), 133.58 (d, J=19.8 Hz), 131.84 (s), 128.49 (s), 128.26 (d, J=7.0 Hz), 126.26 (d, J=2.8 Hz), 125.62 (s), 120.66 (s), 116.93 (d, J=13.4 Hz), 71.12 (s), 29.48 (s); $^{31}$P NMR (162 MHz, CDCl$_3$) δ −18.50 (s).

AP Ex 6

2,3-dihydrobenzofuran-7-yl)bis(2-methoxyphenyl) phosphine

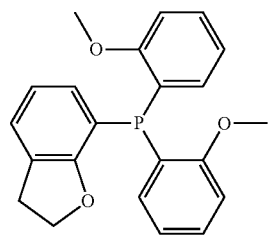 [SMILES: COc1ccccc1P(c1ccccc1OC)c1cccc2c1OCC2]

Repeat AP Ex 4, but with changes: add 7-bromo-2,3-dihydrobenzofuran (350 mg, 1.76 mmol), rather than 8-bromochroman, and add chlorobis(2-methoxyphenyl)phosphine (444 mg, 1.76 mmol) as a suspension in THF (12 mL) to produce AP Ex 6 in white crystalline form (192 mg, 33% yield).

Analyze AP Ex 6 by $^1$H, $^{13}$C, and $^{31}$P NMR spectroscopy to confirm formation. $^1$H NMR (400 MHz, CDCl$_3$) δ 7.33 (t, J=7.7 Hz, 1H), 7.18 (d, J=7.2 Hz, 1H), 6.92-6.81 (m, 2H), 6.77-6.69 (m, 1H), 6.56-6.48 (m, 1H), 4.52 (t, J=8.7 Hz, 1H), 3.74 (s, 3H), 3.21 (t, J=8.7 Hz, 1H). $^{13}$C NMR (101 MHz, CDCl$_3$) δ 162.76 (d, J=18.1 Hz), 161.52 (d, J=16.5 Hz), 133.72 (s), 132.12 (s), 130.04 (s), 126.08 (d, J=2.8 Hz), 125.28 (s), 124.02 (d, J=12.6 Hz), 120.88 (s), 120.53 (s), 116.39 (d, J=14.2 Hz), 110.23 (s), 71.11 (s), 55.72 (s), 29.74 (s). $^{31}$P NMR (162 MHz, CDCl$_3$) δ −40.23 (s).

AP Ex 7 chroman-8-yldiphenylphosphine

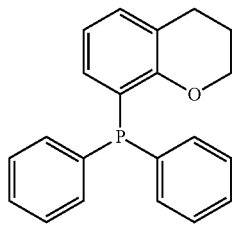 [SMILES: c1ccc(P(c2ccccc2)c2cccc3c2OCCC3)cc1]

Repeat AP Ex 4, but with changes: add 8-bromochroman (500 mg, 2.35 mmol) and add chlorodiphenylphosphine (0.434 mL, 2.35 mmol), neat, rather than chlorobis(2-methoxyphenyl)phosphine to produce AP Ex 7 in white crystalline form (429 mg, 57% yield).

Analyze AP Ex 7 by $^1$H, $^{13}$C, and $^{31}$P NMR spectroscopy to confirm formation. $^1$H NMR (400 MHz, CDCl$_3$) δ 7.40-7.24 (m, 10H), 7.06 (d, J=7.4 Hz, 1H), 6.75 (t, J=7.5 Hz, 1H), 6.52-6.41 (m, 1H), 4.13 (apparent t, J=5.1 Hz, 1H), 2.82 (t, J=6.5 Hz, 1H), 2.06-1.87 (m, 1H); $^{13}$C NMR (101 MHz, CDCl$_3$) δ 156.64 (d, J=15.5 Hz), 136.96 (d, J=10.3 Hz), 133.92 (d, J=20.0 Hz), 131.47 (s), 130.83 (s), 128.53 (s), 128.35 (d, J=7.0 Hz), 124.55 (d, J=11.5 Hz), 121.75 (s), 120.28 (s), 66.80 (s), 24.97 (s), 22.27 (s); $^{31}$P NMR (162 MHz, CDCl$_3$) δ −15.91 (s).

AP Ex 8 bis(2-methoxyphenyl)(2,3,4,5-tetrahydrobenzo[b]oxepin-9-yl)phosphine

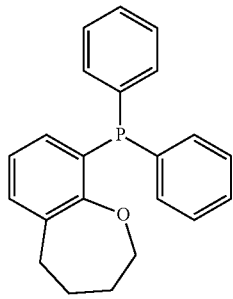 [SMILES: c1ccc(P(c2ccccc2)c2cccc3c2OCCCC3)cc1]

Repeat AP Ex 4, but with changes: add: 9-bromo-2,3,4,5-tetrahydrobenzo[b]oxepine (200 mg, 0.88 mmol), rather than 8-bromochroman and add chlorodiphenylphosphine (0.19 mL, 1.01 mmol), neat, rather than chlorobis(2-methoxyphenyl)phosphine to produce AP Ex 8.

Analyze AP Ex 8 by $^1$H, $^{13}$C, and $^{31}$P NMR spectroscopy to confirm formation. $^1$H NMR (400 MHz, CDCl$_3$) δ 7.53-7.44 (m, 10H), 7.28 (d, J=7.3 Hz, 1H), 7.03 (t, J=7.5 Hz, 1H), 6.71 (ddd, J=7.5, 3.9, 1.6 Hz, 1H), 3.77 (apparent t, J=5.0 Hz, 2H), 2.97 (dd, J=13.8, 8.3 Hz, 2H), 2.05-1.95 (m, 2H), 1.86-1.76 (m, 2H); $^{13}$C NMR (101 MHz, CDCl$_3$) δ 162.39 (d, J=16.6 Hz), 137.50 (d, J=11.0 Hz), 136.76-136.42 (m), 135.79 (d, J=1.0 Hz), 134.47 (d, J=20.4 Hz), 131.75 (s), 131.36 (s), 130.77 (d, J=9.2 Hz), 129.00 (s), 128.73 (d, J=7.1 Hz), 123.87 (s), 73.29 (s), 34.68 (d, J=1.2 Hz), 32.48 (s), 26.48 (s); $^{31}$P NMR (162 MHz, CDCl$_3$) δ −17.65 (s).

AP Ex 9 tris(2,3-dihydrobenzofuran-7-yl)phosphine

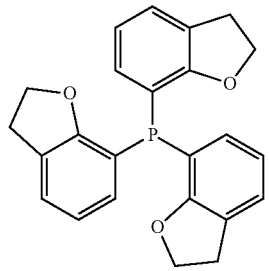 [SMILES: c1cc2c(c(P(c3cccc4c3OCC4)c3cccc4c3OCC4)c1)OCC2]

Repeat AP Ex 4, but with changes: add 7-bromo-2,3-dihydrobenzofuran (1.09 g, 5.49 mmol), rather than 8-bromochroman and add phosphorus trichloride (0.48 mL, 5.49 mmol), neat, rather than chlorobis(2-methoxyphenyl)phosphine to produce AP Ex 9 in white crystalline form (356 mg, 53% yield).

Analyze AP Ex 9 by $^1$H and $^{31}$P NMR spectroscopy to confirm formation. $^1$H NMR (400 MHz, CDCl$_3$) δ 7.18 (dd, J=7.2, 1.2 Hz, 1H), 6.75 (t, J=7.4 Hz, 1H), 6.65-6.57 (m, 1H), 4.53 (t, J=8.7 Hz, 3H), 3.20 (t, J=8.7 Hz, 3H); $^{31}$P NMR (162 MHz, CDCl$_3$) δ −45.71 (d, J=34.6 Hz).

AP Ex 10

P,P'-(9,9-Dimethyl-9H-xanthene-4,5-diyl)bis[bis(2,3-dihydrobenzofuran-7-yl)phosphine)

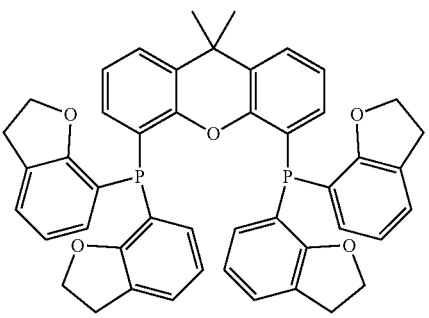 [SMILES: CC1(C)c2cccc(P(c3cccc4c3OCC4)c3cccc4c3OCC4)c2Oc2c(P(c3cccc4c3OCC4)c3cccc4c3OCC4)cccc21]

In a N$_2$-purged dry box, add P,P'-(9,9-Dimethyl-9H-xanthene-4,5-diyl)bis[N,N,N',N'-tetraethyl-phosphonous diamide] (0.944 g, 1.69 mmol) to a glass jar. Dissolve the contents of the glass jar by adding toluene (60 mL). Place the glass jar in a N2-purged dry box freezer at −35° C. for 30 min to cool the pale yellow solution. Remove the glass jar from the dry box freezer and add hydrogen chloride (2.0 M solution in diethyl ether, 9.0 mL) to the contents of the glass jar and stir for one hr at 23° C. to form a white precipitate. Remove an aliquot of the contents of the glass jar, filter, and analyze by $^{31}$P NMR spectroscopy. A single peak at 156 ppm confirmed formation of the desired P,P'-(9,9-Dimethyl-9H-xanthene-4,5-diyl)bis(dichlorophosphine). Filter the contents of the glass jar through Celite and pump down to dryness to produce a sticky white residue. Triturate the sticky white residue with hexanes (40 mL) to produce a white solid. Suspend the white solid in hexanes (40 mL) and filter. Dry the white solid under vacuum for 30 min at 23° C. to produce P,P'-(9,9-Dimethyl-9H-xanthene-4,5-diyl)bis(dichlorophosphine) (0.455 g, 1.10 mmol, 65% yield).

Add dihydrobenzofuran (2.60 g) to a second glass jar with a PTFE-coated stirbar. Stir the contents of the second glass jar and add diethyl ether (40 mL) to dissolve the dihydrobenzofuran. Add n-BuLi (9.0 mL of a 2.5 M solution in hexanes) to the contents of the second glass jar and stir for 48 hrs at 23° C. to produce an orange solution and light orange precipitate. Pump the contents of the glass jar down to dryness to produce a red oil. Add hexanes (20 mL) to the red oil in the second glass jar and stir to produce a light orange solid precipitate. Decant the hexanes from the light orange solid and wash the light orange solid in hexanes (20 mL). Collect the light orange solid by filtration and dry under vacuum for 1 hr at 23° C. to produce impure aryllithium salt (0.99 g).

Add a portion of the light orange solid (0.55 g) and THF (30 mL) to a third glass jar to dissolve the light orange solid and cool the contents of the third glass jar in a dry box freezer at −35° C. for 1 hr. Add P,P'-(9,9-Dimethyl-9H-xanthene-4,5-diyl)bis(dichlorophosphine) from the previous step (0.455 g, 1.10 mL) and THF (40 mL) to a fourth glass jar and cool in the dry box freezer at −35° C. for 1 hr. Remove the third and fourth glass jars from the freezer. Add the contents of the third glass jar dropwise to the contents of the fourth glass jar, while stirring. Allow the contents of the fourth glass jar to warm to 23° C. while stirring for 1 hr. Remove an aliquot of the contents of the fourth glass jar and analyze by $^{31}$P NMR spectroscopy. The spectrum revealed incomplete conversion to the desired AP Ex 10. Add an additional portion of the light orange solid (0.30 g) to the contents of the fourth jar, while stirring. Remove an aliquot of the contents of the fourth jar and analyze by $^{31}$P NMR spectroscopy. A single peak at −39 ppm confirmed formation of the desired AP Ex 10.

Quench the reaction mixture with MeOH (2 mL) and pump down to dryness to produce off-white residue. Suspend off-white residue in MeOH (20 mL) for 1 hr at 60° C., filter, and dry under vacuum for 1 hr at 23° C. to produce sticky solids. Dissolve the sticky solids in toluene (40 mL) and filter through fritted glass funnel Pump filtrate down to dryness to form off-white residue. Triturate off-white residue with hexanes (40 mL) to produce off-white powder. Suspend off-white powder in hexanes (40 mL), filter, and dry under vacuum for 1 hr at 23° C. to yield AP Ex 10 (0.327 g, 0.438 mmol, 40% yield). Analyze AP Ex 10 by $^1$H, $^{13}$C, and $^{31}$P NMR spectroscopy to confirm formation. $^1$H NMR (400 MHz, C$_6$D$_6$) δ 7.22-7.17 (m, 4H), 7.16 (brs, 2H), 7.09 (dd, J=7.6 Hz, J=1.6 Hz, 2H), 6.91 (dd, J=7.2 Hz, J=1.2 Hz, 4H), 6.85 (t, J=7.6 Hz, 2H), 6.71 (t, J=7.6 Hz, 4H), 4.06-3.89 (m, 8H), 2.58-2.49 (m, 8H), 1.34 (s, 6H); $^{13}$C{$^1$H}NMR (101 MHz, C$_6$D$_6$) δ 163.7 (t, J=8.0 Hz, Ar), 153.7 (t, J=10.2 Hz, Ar) 133.5 (t, J=4.3 Hz, ArH), 133.2 (s, ArH), 130.2 (m, Ar), 126.8 (s, ArH), 126.7 (m, Ar), 125.5 (s, ArH), 123.6 (s, ArH), 121.1 (s, ArH), 118.1 (d, J=18.3 Hz), 118.1 (d, J=3.4 Hz), 71.0 (s, CH$_2$), 34.8 (s, C), 32.5 (s, CH$_2$), 30.1 (s, CH$_3$); $^{31}$P{$^1$H}NMR (162 MHz, C$_6$D$_6$) δ −38.5 (s) ppm.

AP Ex 11 bis(2,3-dihydrobenzofuran-7-yl))chlorophosphine

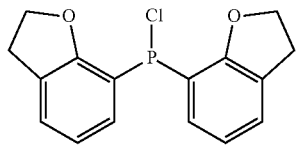 [SMILES: ClP(c1cccc2c1OCC2)c1cccc2c1OCC2]

Add dihydrobenzofuran (2.60 g) and a PTFE-coated stirbar to a glass jar in an N$_2$-purged dry box. Stir the contents of the glass jar and add diethyl ether (40 mL) to dissolve the dihydrobenzofuran. Add n-BuLi (9.0 mL of a 2.5 M solution in hexanes) to the contents of the glass jar and stir for 48 hrs at 23° C. to form a light orange precipitate. Filter the contents of the glass jar and pump to dryness to produce a red oil. Add hexanes (20 mL) to the red oil and stir to produce a light orange solid precipitate. Decant the hexanes from the light orange solid and wash with hexanes (20 mL), filter, and dry under vacuum for 1 hr at 23° C. to produce impure aryllithium salt (0.75 g). Dissolve a portion of the impure aryllithium salt (0.69 g) with THF (50 mL) in a second glass jar and cool in dry box freezer at −35° C. for 1 hr. Add dimethylphosphoramidous dichloride (0.30 mL, 2.6 mmol) dropwise to the contents of the second glass jar. Allow the contents of the second glass jar to warm to 23° C. and stir for one hr. Remove an aliquot of the contents of the second glass jar and analyze by $^{31}$P NMR spectroscopy. The spectrum showed conversion to the desired bis(2,3-dihydrobenzofuran-2-yl)dimethylaminophosphine (46.8 ppm, 82% yield). The (2,3-dihydrobenzofuran-7-71)(dimethylamino)chlorophosphine was also present as an impurity (125.5 ppm, 14%).

Pump down the reaction mixture to dryness and triturate with hexanes (40 mL) to produce white residue. Slurry white residue in toluene (60 mL) with stirring and filter through Celite to remove LiCl. Place toluene filtrate in a third glass jar in a dry box freezer at −35° C. for 30 min. Add hydrogen chloride (2.0 M solution in diethyl ether, 2.8 mL) to the contents of the third glass jar while stirring. Allow the contents of the third glass jar to warm to 23° C. and stir for one hr to form white precipitate. Remove an aliquot of the reaction mixture, filter, and analyze by $^{31}$P NMR spectroscopy. The spectrum showed conversion to the desired AP Ex 11 (66 ppm). Filter the reaction mixture through Celite and pump down to dryness. Triturate resultant yellow oil in hexanes (40 mL) to produce an off-white solid. Slurry off-white solid in hexanes (40 mL) with stirring, collect by filtration and dry under vacuum for 1 hr at 23° C. to produce AP Ex 11 (0.171 g, 0.561 mmol, yield 22%).

Analyze AP Ex 11 by $^1$H, $^{13}$C, and $^{31}$P NMR spectroscopy to confirm formation. $^1$H NMR (400 MHz, C$_6$D$_6$) δ 7.61-7.57 (m, 2H), 6.84 (dq, J=7.6 Hz, J=1.2 Hz, 2H), 6.73 (t, J=8.0 Hz, 2H), 3.87 (t, J=8.8 Hz, 4H), 2.35 (t, J=8.8 Hz, 4H); $^{13}$C{$^1$H}NMR (101 MHz, C$_6$D$_6$) δ 163.0 (d, J=20.0 Hz, Ar), 131.5 (d, J=7.3 Hz, ArH), 127.7 (d, J=1.7 Hz, Ar), 127.6 (s, ArH) 121.3 (s, ArH), 118.6 (d, J=38.0 Hz, Ar), 71.8 (s, CH$_2$), 29.5 (s, $CH_2$); $^{31}P\{^1H\}$ NMR (162 MHz, $C_6D_6$) δ 66.6 (s) ppm.

Transition Metal Complexes (TMC)

TMC Ex 1

Acetylacetonato[dicyclohexyl(2,3-dihydrobenzofuran-7-yl)phosphine]rhodium(I)

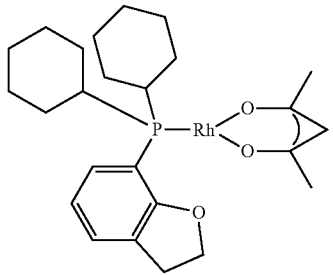

Prepare TMC Ex 1 as follows: Add AP Ex 3 (0.039 g, 0.12 mmol) to a glass vial in a $N_2$-purged dry box. Add $C_6D_6$ (1 mL) to the glass vial to completely dissolve AP Ex 3. In a second glass vial, add acetylacetonatodicarbonylrhodium(I) (0.032 g, 0.12 mmol). Add the contents of the first glass vial to the second glass vial to produce a yellow solution. Note evolution of CO gas from solution, indicating formation of a phosphine-rhodium complex. Transfer solution in glass vial to NMR tube and analyze by $^1H$ and $^{31}P$ NMR spectroscopy. $^{31}P$ NMR indicates near quantitative conversion (>97%) to TMC Ex 1. Return NMR sample to $N_2$-purged dry box and transfer to a third glass vial. Use 3 mL of THF to wash out NMR tube and transfer washings to vial. Remove solvent under vacuum. Add 2 mL of hexanes to vial and remove solvent under vacuum. Repeat. Slurry resultant pale yellow powder in 1 mL of hexanes and place in dry box freezer at −35° C. for 1 hour. Collect pale yellow powder by filtration and dry under vacuum for 1 hour to yield TMC Ex1 (0.020 g, 0.039 mmol, 31%).

Analyze TMC Ex 1 by $^1H$, $^{13}C$, and $^{31}P$ NMR spectroscopy to confirm formation. $^1H$ NMR (400 MHz, $C_6D_6$) δ 8.25 (dd, J=7.2 Hz, J=12.0 Hz, 1H), 6.86 (m, 1H), 6.76 (td, J=0.8 Hz, J=7.6 Hz, 1H), 5.38 (s, 1H), 3.91 (t, J=8.8 Hz, 2H), 2.92 (m, 2H), 2.42 (t, J=8.8 Hz, 2H), 2.24 (m, 2H), 1.97 (s, 3H), 1.95 (m, 2H), 1.78 (s, 3H), 1.74-1.55 (m, 10H), 1.42-1.23 (m, 4H), 1.08 (m, 2H); $^{13}C\{^1H\}$NMR (101 MHz, $C_6D_6$) δ 191.5 (dd, J=23.5 Hz, J=77.0 Hz), 188.5 (s), 184.7(s), 161.9 (s), 140.1 (d, J=17.9 Hz), 127.7 (d, J=2.2 Hz), 127.3 (d, J=4.1 Hz), 120.6 (d, J=11.3 Hz), 111.2 (d, J=43.0 Hz), 101.0 (d, J=2.3 Hz), 71.3 (s), 33.7 (s), 33.4 (s), 30.3 (d, J=3.7 Hz), 29.6 (s), 29.2 (d, J=1.9 Hz), 28.1 (dd, J=1.0 Hz, J=5.2 Hz), 27.9 (d, J=4.3 Hz), 27.8 (d, J=7.8 Hz), 27.5 (m), 27.0 (d, J=1.3 Hz); $^{31}P\{^1H\}$NMR (162 MHz, $C_6D_6$) δ 64.3 (d, J=174.6 Hz) ppm.

TMC Ex 2 allyl[di-tert-butyl(2,3-dihydrobenzofuran-7-yl)phosphine]palladium(II) chloride

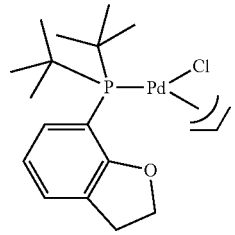

Prepare TMC Ex 2 as follows: Add AP Ex 1 (0.051 g, 0.19 mmol) to a glass vial in a $N_2$-purged dry box. Add $C_6D_6$ (1 mL) to the glass vial to completely dissolve AP Ex 1. In a second glass vial, add allylpalladium(II) chloride dimer (0.035 g, 0.096 mmol). Add the contents of the first glass vial to the second glass vial to produce a yellow solution. Transfer solution in glass vial to NMR tube and analyze by $^1H$ and $^{31}P$ NMR spectroscopy. $^{31}P$ NMR indicates quantitative conversion to TMC Ex 2. Return NMR sample to $N_2$-purged dry box and transfer to a third glass vial. Use 5 mL of THF to wash out NMR tube and transfer washings to vial. Remove solvent under vacuum. Add 2 mL of hexanes to vial and remove solvent under vacuum. Slurry resultant yellow powder in 1 mL of hexanes and collect powder by filtration. Dry yellow powder under vacuum for 1 hour to yield TMC Ex 2 (0.039 g, 0.087 mmol, 91%).

Analyze TMC Ex 1 by $^1H$, $^{13}C$, and $^{31}P$ NMR spectroscopy to confirm formation. $^1H$ NMR (400 MHz, $CD_2Cl_2$) δ 7.48 (m, 1H), 7.28 (m, 1H), 6.85 (t, J=7.2 Hz, 1H), 5.48 (m, 1H), 4.51 (m, 3H), 3.60 (dd, J=9.2 Hz, J=13.6 Hz, 1H), 3.34 (br s, 1H), 3.22 (t, J=8.4 Hz, 2H), 2.67 (br s, 1H), 1.42 (br s, 18H); $^{13}C\{^1H\}$NMR (101 MHz, $CD_2Cl_2$) δ 161.1 (s), 137.1 (br s), 127.8 (d, J=2.9 Hz), 127.1 (d, J=1.8 Hz), 119.3 (d, J=10.2 Hz), 115.0 (d, J=4.7 Hz), 112.9 (d, J=24.5 Hz), 78.8 (d, J=29.7 Hz), 70.7 (s), 58.3 (s), 36.4 (br s), 29.7 (br d, J=94.8 Hz), 29.4 (s); $^{31}P\{^1H\}$ NMR (162 MHz, $CD_2Cl_2$) δ 77.7 (br s) ppm.

Butadiene Telomerization (BT)

BT Ex 1 with AP Ex 5

In a glovebox, dissolve degassed glacial acetic acid (AcOH) (55.3 µL) in degassed MeOH to a volume of 5 mL (0.1932 M AcOH in MeOH) to form AcOH solution. Dissolve palladium(II) acetylacetonate (Pd(acac)$_2$) (0.0147 g, 0.0000483 moles), AP Ex 5 and 0.25 mL of the AcOH solution in MeOH to a total volume of 25 mL to form precatalyst stock solution. Add dibutyl ether ($Bu_2O$, 5 mL), MeOH (10.96 mL), anhydrous degassed methylcyclohexane (MeCy, 1.6 mL), the precatalyst stock solution (1 mL), and a portion of a solution of sodium methoxide (NaOMe) (1.0 mL) in MeOH (0.01932 M) to a Fisher-Porter bottle. In general, the reactions were conducted with MeOH (12.8M). Seal the Fisher-Porter bottle with a valve equipped with a septum port. Distill butadiene (5 mL) outside of the glovebox into a gas-tight syringe. Determine the mass of butadiene by weighing the syringe before and after addition to the Fisher-Porter bottle. Inject the butadiene into the Fisher-Porter bottle with the needle placed below the surface of the solution (5 mL, with the precise weight for each run being calculated by weighing the syringe before and after injection and taking the difference of the two). Place the reactor in an oil bath heated to 60° C. with stirring and react for a 4 hrs. Remove aliquots through a 24" needle equipped with a gas-tight valve and perform GC analysis.

BT Ex 2 with AP Ex 5
Repeat BT Ex 1, but with changes: heat the oil bath to 90° C.

BT Ex 3 with AP Ex 5
Repeat BT Ex 1, but with changes: heat the oil bath to 40° C.

BT Ex 4 with AP Ex 4
Repeat BT Ex 3, but with changes: use AP Ex 4 rather than AP Ex 5.

BT Ex 5 with AP Ex 4
Repeat BT Ex 1, but with changes: use AP Ex 4 rather than AP Ex 5.

BT Ex 6 with AP Ex 6
Repeat BT Ex 1, but with changes: use AP Ex 6 rather than AP Ex 5.

BT Ex 7 with AP Ex 6
Repeat BT Ex 2, but with changes: use AP Ex 6 rather than AP Ex 5.

BT Ex 8 with AP Ex 7
Repeat BT Ex 1, but with changes: use AP Ex 7 rather than AP Ex 5.

BT Ex 9 with AP Ex 7
Repeat BT Ex 2, but with changes: use AP Ex 7 rather than AP Ex 5.

BT Ex 10 with AP Ex 9
Repeat BT Ex 3, but with changes: use AP Ex 9 rather than AP Ex 5.

BT Ex 11 with AP Ex 9
Repeat BT Ex 1, but with changes: use AP Ex 9 rather than AP Ex 5.

BT Ex 12 with AP Ex 6
Repeat BT Ex 3, but with changes: use AP Ex 6 rather than AP Ex 5.

Comp Ex 1 with tris(2-methoxyphenyl)phosphine
Repeat BT Ex 2, but with changes: use tris(2-methoxyphenyl)phosphine rather than AP Ex 5.

Comp Ex 2 with (2-methoxyphenyl)diphenylphosphine
Repeat BT Ex 2, but with changes: use (2-methoxyphenyl)diphenylphosphine rather than AP Ex 5.

The conversion (Conv) is the moles of butadiene converted divided by the moles of butadiene fed into the reactor. MOD-1 (1-methoxy-2,7-octadiene) is the moles of MOD-1 divided by the moles of all products produced. MOD-3 (3-methoxy-1,7-octadiene) is the moles of MOD-3 divided by the moles of all products. The L/B ratio is the moles of MOD-1 divided by the moles of MOD-3. Catalyst efficiency is the grams of MOD-1 divided by the grams of Pd divided by the hrs of reaction time. Data for tris(2-methoxyphenyl)phosphine (Comp Ex 1) and (2-methoxylphenyl)diphenylphosphine (Comp Ex 2) are from WO2010/019360(A2) and are included as comparative examples.

TABLE 1

| Example | Temperature (° C.) | Conv (mol %) | MOD-1 (mol %) | MOD-3 (mol %) | L/B ratio | Catalyst Efficiency |
|---|---|---|---|---|---|---|
| BT Ex 1 | 60 | 89.3 | 95.1 | 4.0 | 23.8 | 4845 |
| BT Ex 2 | 90 | 77.2 | 92.3 | 5.1 | 18.1 | 4357 |
| BT Ex 3 | 40 | 60.4 | 96.4 | 3.1 | 31.1 | 3061 |
| BT Ex 4 | 40 | 8.1 | 97.7 | 2.3 | 42.5 | 303 |
| BT Ex 5 | 60 | 7.0 | 96.9 | 3.1 | 31.3 | 394 |
| BT Ex 6 | 60 | 17.0 | 97.3 | 3.1 | 36.0 | 860 |
| BT Ex 7 | 90 | 8.4 | 96.5 | 3.5 | 27 | 490 |
| BT Ex 8 | 60 | 47.6 | 95.1 | 4.0 | 23.8 | 2656 |
| BT Ex 9 | 90 | 65.3 | 92.6 | 5.2 | 18.0 | 3602 |
| BT Ex 10 | 40 | 22.3 | 98.0 | 2.0 | 49.0 | 1429 |
| BT Ex 11 | 60 | 32.3 | 97.3 | 2.7 | 36.037 | 1890 |
| BT Ex 12 | 40 | 11.3 | 97.7 | 2.3 | 42.5 | 599 |
| Comp Ex 1 | 90 | 4.1 | 86.1 | 2.6 | 33 | 194 |
| Comp Ex 2 | 90 | 65.6 | 93.6 | 3.9 | 24 | 3363 |

The data in Table 1 shows the telomerization of butadiene with AP Ex 4, 5, 6, 7 and 9. The table also includes data for tris(2-methoxyphenyl)phosphine as Comp Ex 1 and (2-methoxyphenyl)diphenylphosphine as Comp Ex 2. It is demonstrated that replacing an ortho-methoxyphenyl with a fused ring ortho-alkoxy substitution in some cases can increase the catalyst efficiency. For example, BT Ex 2 demonstrates an increase in catalyst efficiency compared to Comp Ex 2; BT Ex 11 demonstrates an increase in catalyst efficiency compared to Comp Ex 1, and BT Ex 10 demonstrates an increase in catalyst efficiency compared to BT Ex 12.

What is claimed is:

1. An aryl phosphine of Formula (I):

$$\text{(I)}$$

where n is an integer in a range from 1 to 3, where $R^1$ and $R^3$ are independently selected from the group consisting of H, a substituted or unsubstituted alkyl having 1 to 18 carbons, and a substituted or unsubstituted phenyl ring, where each $R^2$ and $R^{2'}$ is independently selected from the group consisting of H, a substituted or unsubstituted alkyl having 1 to 18 carbons, and a substituted or unsubstituted phenyl ring, where $R^4$, $R^5$, $R^6$, and $R^7$ are independently selected from the group consisting of H, a substituted or unsubstituted alkyl having 1 to 18 carbons, a substituted or unsubstituted cycloalkyl having 3 to 18 carbons, a halogen, and a substituted or unsubstituted phenyl ring, where permissible substituents on $R^1$, $R^2$, $R^{2'}$, $R^3$, $R^4$, $R^5$, $R^6$, and $R^7$ are functional groups that include heteroatoms selected from the group consisting of oxygen, nitrogen, halogens, sulfur, boron, phosphorus, and silicon.

2. The aryl phosphine of claim 1, wherein $R^4$ and $R^5$ are independently selected from the group consisting of methyl, ethyl, n-propyl, isopropyl, n-butyl, sec-butyl, isobutyl, t-butyl, adamantyl, phenyl, biphenyl, and cyclohexyl.

3. The aryl phosphine of claim 1, where $R^4$ and $R^5$ together with the phosphorus atom form a 5-, 6-, or 7-membered ring.

4. The aryl phosphine of claim 1, where $R^4$ and $R^5$ are independently selected from the group consisting of Formula (II) to (X):

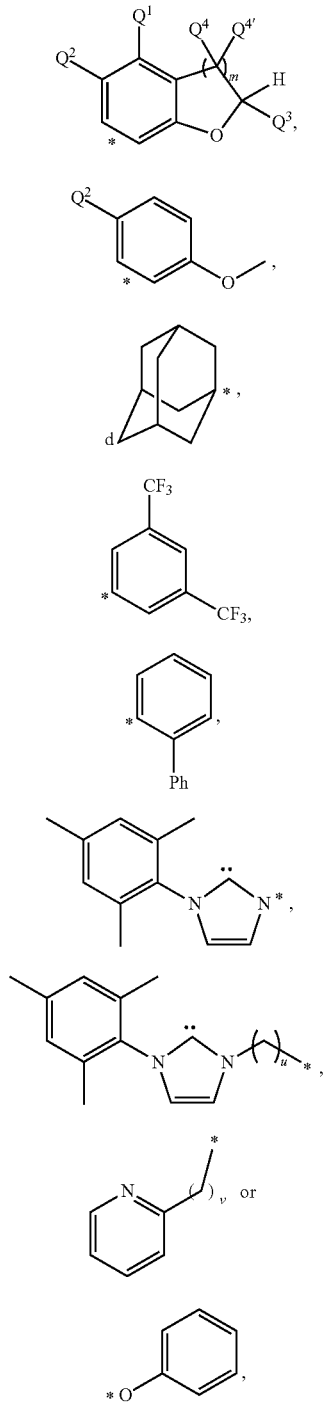

where m is 1 or 2, where $Q^1$, $Q^2$, and $Q^5$ are independently selected from the group consisting of H, a substituted or unsubstituted alkyl having 1 to 18 carbons, a substituted or unsubstituted cycloalkyl having 3 to 18 carbons, a halogen, and a substituted or unsubstituted phenyl ring, $Q^3$ is selected from the group consisting of H, a substituted or unsubstituted alkyl having 1 to 18 carbons, and a substituted or unsubstituted phenyl ring, each $Q^4$ and $Q^{4'}$ is independently selected from the group consisting of H, a substituted or unsubstituted alkyl having 1 to 18 carbons, and a substituted or unsubstituted phenyl ring, where u is an integer in a range from 0 to 2, where v is an integer in a range from 0 to 2, and where when $R^4$ and $R^5$ are both Formula (X), $R^4$ and $R^5$ are optionally covalently bound together at the ortho position to the respective C atoms in Formula (X).

5. The aryl phosphine of claim 1, where the aryl phosphine is selected from the group consisting of:

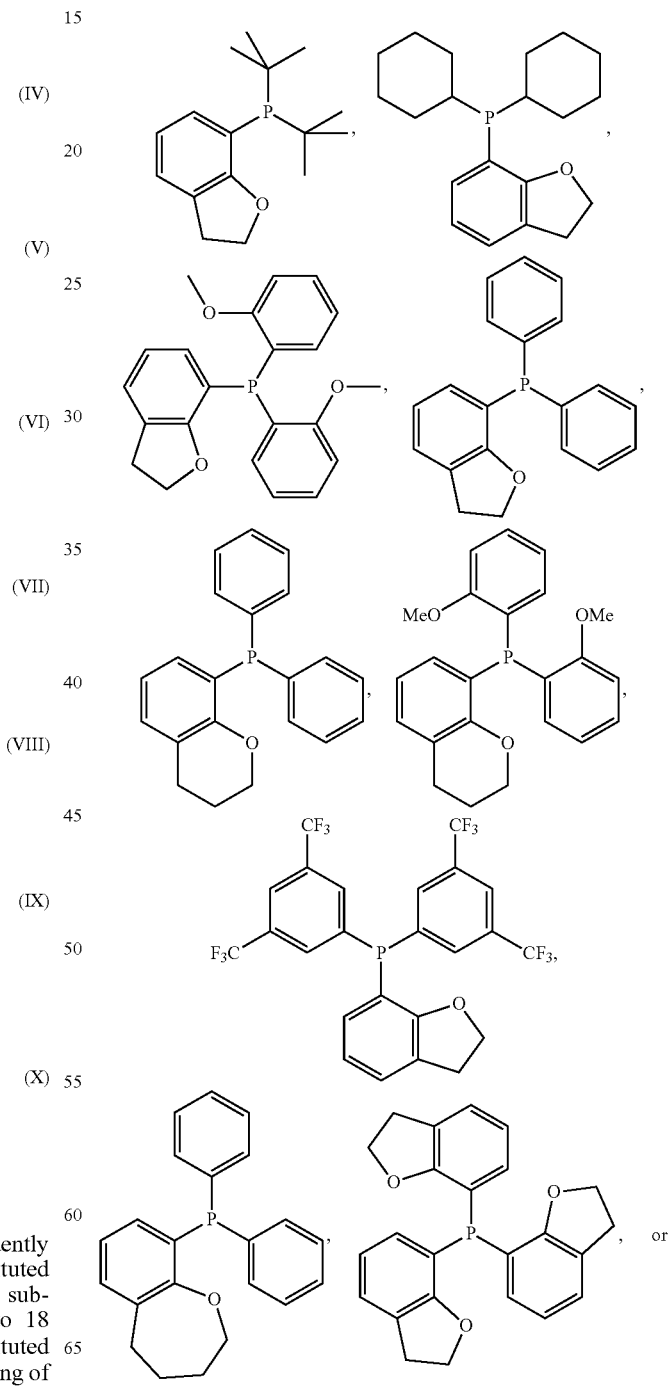

-continued

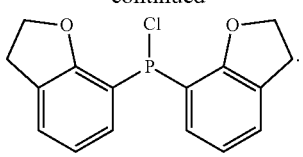

6. An aryl phosphine of Formula (I):

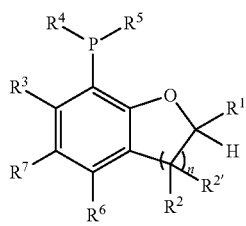
(I)

where n is an integer in a range from 1 to 3, where $R^1$ and $R^3$ are independently selected from the group consisting of H, a substituted or unsubstituted alkyl having 1 to 18 carbons, and a substituted or unsubstituted phenyl ring, where each $R^2$ and $R^{2'}$ is independently selected from the group consisting of H, a substituted or unsubstituted alkyl having 1 to 18 carbons, and a substituted or unsubstituted phenyl ring, where $R^4$ is selected from the group consisting of H, a substituted or unsubstituted alkyl having 1 to 18 carbons, a halogen, a substituted or unsubstituted cycloalkyl having 3 to 18 carbons, and a substituted or unsubstituted phenyl ring, where permissible substituents on $R^1$, $R^2$, $R^{2'}$, $R^3$ $R^4$, $R^6$, and $R^7$ are functional groups that include heteroatoms selected from the group consisting of oxygen, nitrogen, halogen, sulfur, boron, phosphorus, and silicon, and where $R^5$ is a bridging group that includes an aromatic ring and connects the aryl phosphine of Formula (I) to a second phosphine.

7. The aryl phosphine of claim 6, where $R^5$ and the second phosphine together form a structure selected from the group consisting of Formulae (II) to (IV):

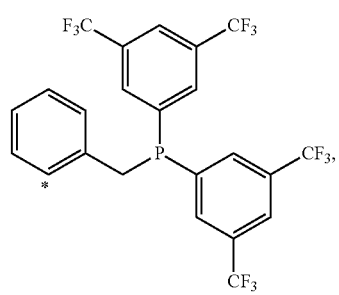
(II)

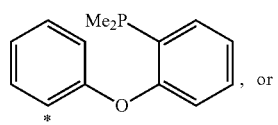
(III)

-continued

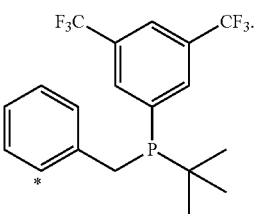
(IV)

8. An aryl phosphine of Formula (I):

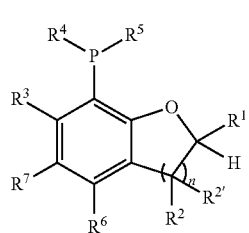
(I)

where n is an integer in a range from 1 to 3, where $R^1$ and $R^3$ are independently selected from the group consisting of H, a substituted or unsubstituted alkyl having 1 to 18 carbons, and a substituted or unsubstituted phenyl ring, where each $R^2$ and $R^{2'}$ is independently selected from the group consisting of H, a substituted or unsubstituted alkyl having 1 to 18 carbons, and a substituted or unsubstituted phenyl ring, where $R^4$ is selected from the group consisting of H, a substituted or unsubstituted alkyl having 1 to 18 carbons, a halogen, a substituted or unsubstituted cycloalkyl having 3 to 18 carbons, and a substituted or unsubstituted phenyl ring, where permissible substituents on $R^1$, $R^2$, $R^{2'}$, $R^4$, $R^6$, and $R^7$ are functional groups that include heteroatoms selected from the group consisting of oxygen, nitrogen, halogen, sulfur, boron, phosphorus, fluorine, and silicon, and where $R^5$ is a bridging group selected from the group consisting of Formulae (II) to (XVII):

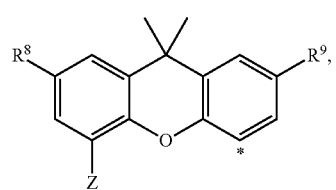
(II)

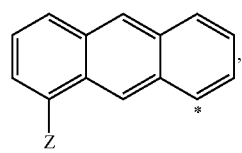
(III)

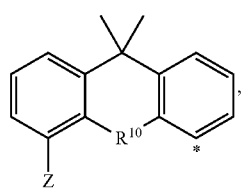
(IV)

-continued

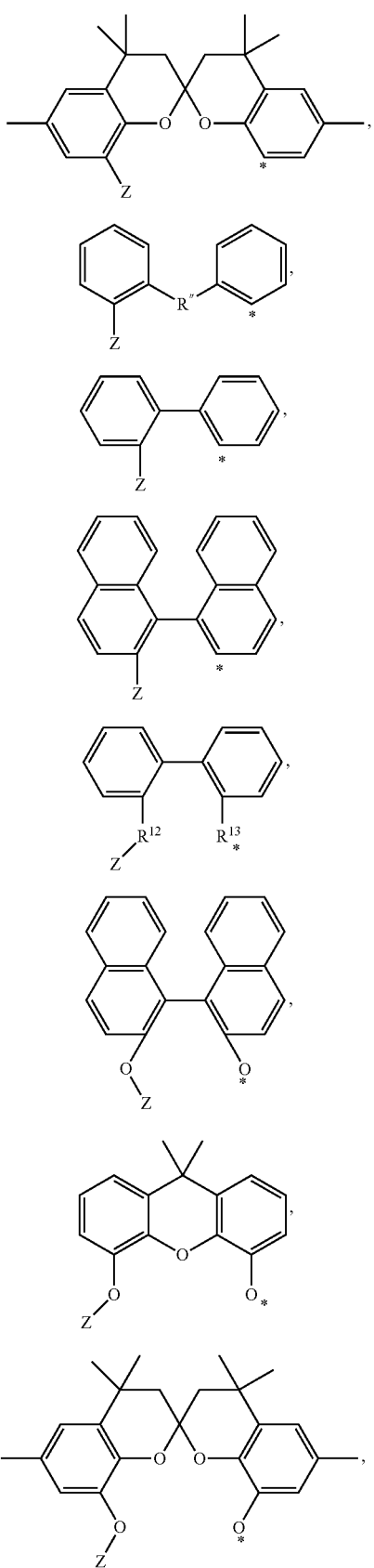

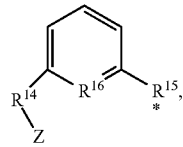

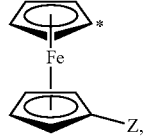

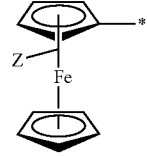

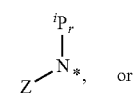

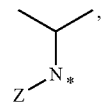

where Z is the aryl phosphine of Formula (I), where $R^8$ and $R^9$ are independently selected from H and an alkyl having 4 carbons, where $R^{10}$ is selected from the group consisting of C and S, where $R^{11}$ is selected from the group consisting of O and S, where $R^{12}$, $R^{13}$, $R^{14}$ and $R^{15}$ are each independently selected from the group consisting of C and O, where $R^{16}$ is selected from the group consisting of N and C, with the proviso that when $R^{16}$ is N then $R^{14}$ and $R^{15}$ are C.

9. The aryl phosphine of claim 8, where the aryl phosphine has the formula:

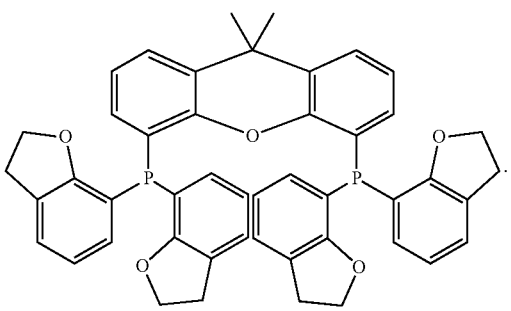 [SMILES: CC1(C)c2cccc(P(c3cccc4c3OCC4)c3cccc4c3OCC4)c2Oc2c(P(c3cccc4c3OCC4)c3cccc4c3OCC4)cccc21]

10. The aryl phosphine of claim 1, where the aryl phosphine is a ligand for a transition metal selected from the group consisting of titanium (Ti), copper (Cu), palladium (Pd), cobalt (Co), rhodium (Rh), ruthenium (Ru), chromium (Cr) and platinum (Pt).

* * * * *